(12) United States Patent
Murphy

(10) Patent No.: US 9,101,431 B2
(45) Date of Patent: Aug. 11, 2015

(54) GUIDE FOR ACETABULAR COMPONENT POSITIONING

(71) Applicant: Stephen B. Murphy, Winchester, MA (US)

(72) Inventor: Stephen B. Murphy, Winchester, MA (US)

( * ) Notice: Subject to any disclaimer, the term of this patent is extended or adjusted under 35 U.S.C. 154(b) by 33 days.

(21) Appl. No.: 13/708,132

(22) Filed: Dec. 7, 2012

(65) Prior Publication Data

US 2013/0165941 A1 Jun. 27, 2013

Related U.S. Application Data

(60) Provisional application No. 61/567,982, filed on Dec. 7, 2011.

(51) Int. Cl.
*A61B 17/88* (2006.01)
*A61F 2/46* (2006.01)
*A61B 19/00* (2006.01)

(52) U.S. Cl.
CPC ........... *A61B 17/8897* (2013.01); *A61B 19/201* (2013.01); *A61F 2/4609* (2013.01); *A61F 2002/4687* (2013.01)

(58) Field of Classification Search
CPC ............. A61B 17/8897; A61B 19/201; A61B 2002/4687
USPC .......................................... 606/86 R, 91, 130
See application file for complete search history.

(56) References Cited

U.S. PATENT DOCUMENTS

| | | | |
|---|---|---|---|
| 5,122,145 A | 6/1992 | Fishbane | |
| 5,141,512 A | 8/1992 | Farmer et al. | |
| 5,327,907 A | 7/1994 | Fischer | |
| 5,376,093 A | 12/1994 | Newman | |
| 5,697,939 A * | 12/1997 | Kubota et al. | 606/130 |
| 5,776,143 A | 7/1998 | Adams | |
| 5,824,007 A | 10/1998 | Faraz et al. | |
| 6,090,114 A | 7/2000 | Matsuno et al. | |
| 6,132,437 A | 10/2000 | Omurtag et al. | |
| 6,290,196 B1 | 9/2001 | Mayenberger | |
| 6,395,005 B1 | 5/2002 | Lovell | |
| 7,419,492 B2 | 9/2008 | Yoon et al. | |
| 8,267,938 B2 | 9/2012 | Murphy | |
| 2003/0153829 A1 | 8/2003 | Sarin et al. | |
| 2004/0210233 A1 | 10/2004 | Yoon et al. | |

(Continued)

FOREIGN PATENT DOCUMENTS

| | | | |
|---|---|---|---|
| JP | 2004-89653 A | 3/2004 |
| JP | 2005-111257 A | 4/2005 |

(Continued)

OTHER PUBLICATIONS

English Description of Japanese Publication No. JP2004-089,653, retrieved on Aug. 27, 2014, pp. 1-30.

(Continued)

*Primary Examiner* — Christopher Beccia
(74) *Attorney, Agent, or Firm* — Cesari and McKenna, LLP

(57) ABSTRACT

Apparatus for aligning a surgical instrument, such as an acetabular cup inserter, with a direction guide that defines an orientation in space for insertion of the cup. The apparatus comprises a parallel guide having a first arm for alignment with the direction guide and a second arm spaced from the first arm but maintained in parallel relationship with it. The cup inserter can be aligned with the first arm by aligning it with the second arm.

11 Claims, 4 Drawing Sheets

(56) References Cited

U.S. PATENT DOCUMENTS

| | | | |
|---|---|---|---|
| 2004/0254586 A1 | 12/2004 | Sarin et al. | |
| 2005/0076441 A1 | 4/2005 | Dominati et al. | |
| 2005/0107799 A1 | 5/2005 | Graf et al. | |
| 2006/0052795 A1 | 3/2006 | White | |
| 2006/0161167 A1 | 7/2006 | Myers et al. | |
| 2006/0225529 A1* | 10/2006 | Fischer et al. | 74/469 |
| 2006/0241441 A1 | 10/2006 | Chinn | |
| 2009/0171370 A1 | 7/2009 | Yoon et al. | |
| 2011/0009778 A1* | 1/2011 | Sarin et al. | 600/595 |
| 2013/0006255 A1 | 1/2013 | Murphy | |

FOREIGN PATENT DOCUMENTS

| | | |
|---|---|---|
| SU | 441 933 | 9/1974 |
| WO | WO-00/30557 | 6/2000 |
| WO | WO-01/34017 | 5/2001 |
| WO | WO-03/009768 | 2/2003 |
| WO | WO-2004/021898 | 3/2004 |
| WO | WO-2005/046451 | 5/2005 |
| WO | WO-2006/109983 | 10/2006 |

OTHER PUBLICATIONS

English Description of Japanese Publication No. JP 2005-111,257, retrieved on Aug. 27, 2014, pp. 1-26.

English Translation of Office Action, from Japanese Patent Office for Japanese Patent Application No. JP 2013-112536, dated Apr. 1, 2014, pp. 1-2.

European Search Report, European Application No. 13153277.2-1659/2626032, Applicant: Stephen B. Murphy, Date of Mailing: Mar. 20, 2014, pp. 1-6.

European Search Report, European Application No. 13153236.8-1659/2626031, Applicant: Stephen B. Murphy, Date of Mailing: Aug. 22, 2014, pp. 1-5.

Notification of Transmittal of the International Search Report and the Written Opinion of the International Searching Authority, or the Declaration, International Filing Date: Oct. 30, 2008, International Application No. PCT/US2008/012300, Applicant: Stephen B. Murphy, Date of Mailing: Mar. 5, 2009, pp. 1-8.

* cited by examiner

GUIDE FOR ACETABULAR COMPONENT POSITIONING

CROSS-REFERENCE TO RELATED APPLICATIONS

The present application claims the benefit of U.S. Provisional Patent Application Ser. No. 61/567,982, which was filed on Dec. 7, 2011, by Stephen B. Murphy for a ADAPTOR FOR ACETABULAR COMPONENT POSITIONING and is hereby incorporated by reference.

This application is related to U.S. patent application Ser. No. 12/134,545, "Method And Apparatus For Determining Acetabular Component Positioning", filed Jun. 6, 2008 by Stephen B. Murphy, claiming priority of U.S. Provisional Patent Application Ser. No. 60/984,425, filed Nov. 1, 2007, and published on Dec. 10, 2009 as U.S. Publication No. US-20090306679-A1, and the entire contents of which are expressly incorporated herein by reference.

BACKGROUND INFORMATION

The above application ("the '545 application") describes a method and apparatus for determining acetabular component positioning, particularly for use in connection with hip arthroplasty. The method establishes a coordinate frame for the ipsilateral hip, and an apparatus is disclosed that rapidly and reliably establishes the desired frame. A preferred form of the apparatus is shown in FIG. 4 of the '545 application, and comprises a manual stereotactic instrument in the form of a tripod having of a pair of extensible arms extending from a common hub about which the arms can be rotated. First and second legs or cannulas, respectively, extend from an end of the respective arms remote from the hub and generally perpendicular to the plane formed by the arms, and a third leg or cannula extends from the hub, also generally perpendicular to that plane. The tips of the legs remote from the plane themselves are then positioned by the surgeon or by the instrument itself.

One of the tips is placed at the root of the ischium, a short distance (e.g., 20 millimeters or so) above the infracotyloid notch; this establishes a "basepoint" of Anchor point for proper docking of the instrument to the hip. A second tip is placed by the surgeon on the lateral side of the iliac wing, adjacent to the anterior superior iliac spine. The third tip then lands on the surface of the lateral ilium, anterior to the sciatic notch; the precise location is determined by the settings of the instrument, in particular, the extensions of the arms and the angle between them. The tips of the three legs, when so positioned, themselves form a plane and provide a reference frame with respect to which the orientation of the hip may be referenced.

As described in the '545 application, an alignment guide in the form of a rod (cf. rod 128 of FIG. 4 of the '545 application) is affixed to the instrument and is set at a defined orientation with respect to the instrument; this orientation defines the orientation at which an acetabular cup is to be inserted into the acetabulum by the surgeon. The insertion is accomplished with the aid of a cup inserter, an instrument onto which an acetabular cup is removably fitted at one end and having a handle at the other end by means of which the surgeon can position the cup and apply force to seat the cup when it is maneuvered into the desired orientation in the acetabulum indicated by the alignment guide. At least a portion of the cup inserter, typically the handle, has a straight segment which can be aligned with the alignment guide rod by visual inspection.

SUMMARY OF THE INVENTION

While the system described above provides a simpler, faster, and generally more accurate procedure for inserting an acetabular cup into the acetabulum with a desired orientation, I have developed a simple instrument for further enhancing the accuracy of the procedure.

In particular, the axis of the handle of the cup inserter, which the surgeon manipulates to align the inserter with the guide rod, is typically spaced at a distance of several inches from the axis of the guide rod, thereby increasing the difficulty of visually aligning the two axes so that they are parallel. To minimize alignment errors that may result from this, I provide a parallel guide that quickly and easily attaches to the instrument guide rod and that provides a second guide rod, parallel to the first, but positionable closer to the handle of the cup inserter so that the surgeon may accurately align the axis of the inserter with that of the instrument guide rod.

Accordingly, it is an object of the invention to enhance the accuracy of acetabular cup alignment in surgical procedures.

Specifically, it is an object of the invention to enhance the accuracy of acetabular cup alignment in hip arthroplasty procedures.

Further, it is an object of the invention to extend the capabilities of the method and apparatus of the '545 application to further enhance the accuracy of acetabular cup alignment in hip arthroplasty procedures.

The foregoing and other and further objects and features of the present invention will be understood on reference to the following detailed description of the invention, when taken in conjunction with the accompanying drawings, in which.

DETAILED DESCRIPTION OF AN ILLUSTRATIVE EMBODIMENT

Figure 1:
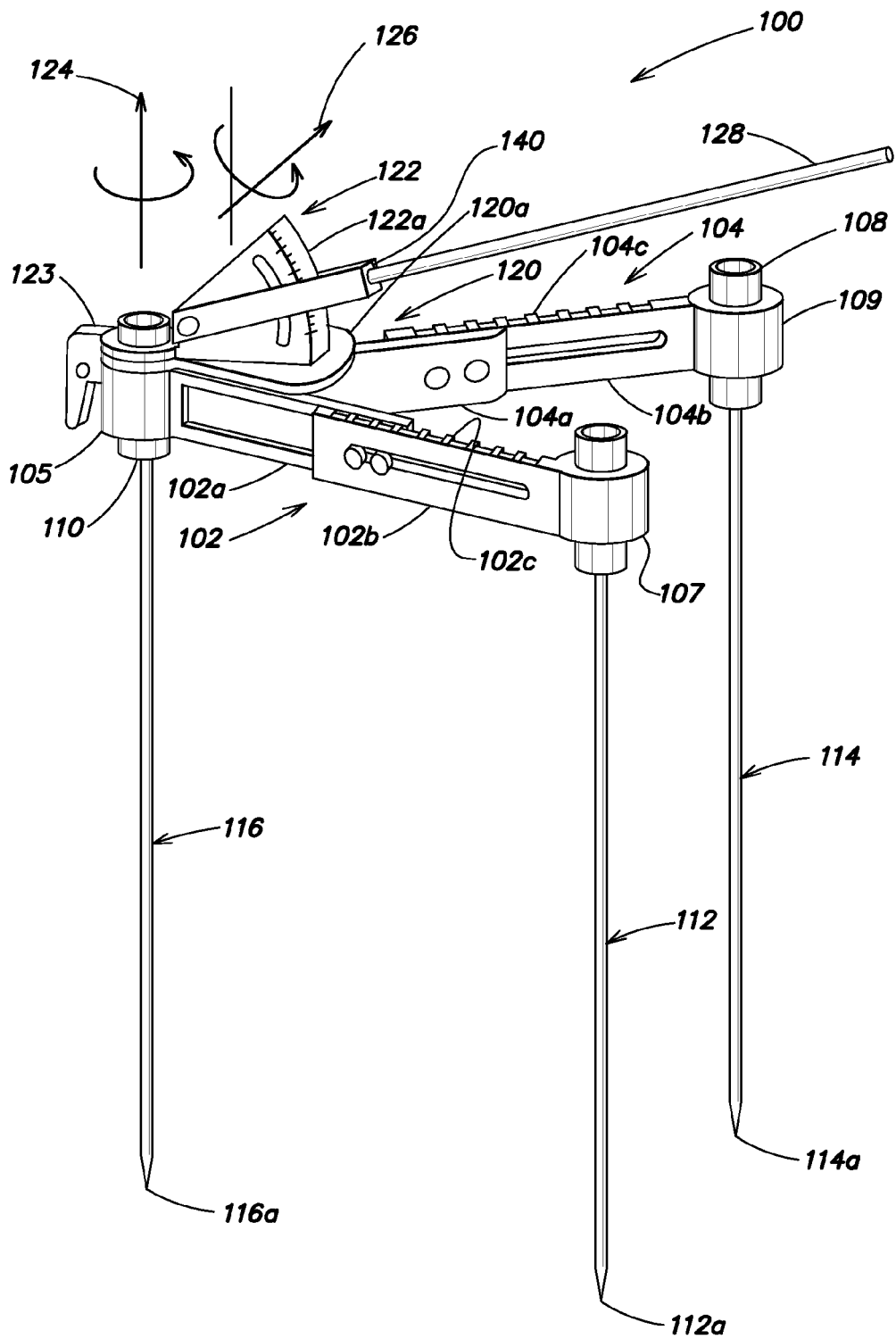
FIG. 1 is a reproduction of FIG. 4 of the '545 application, showing a preferred form of the manual stereotactic instrument of that application.
Figure 4:
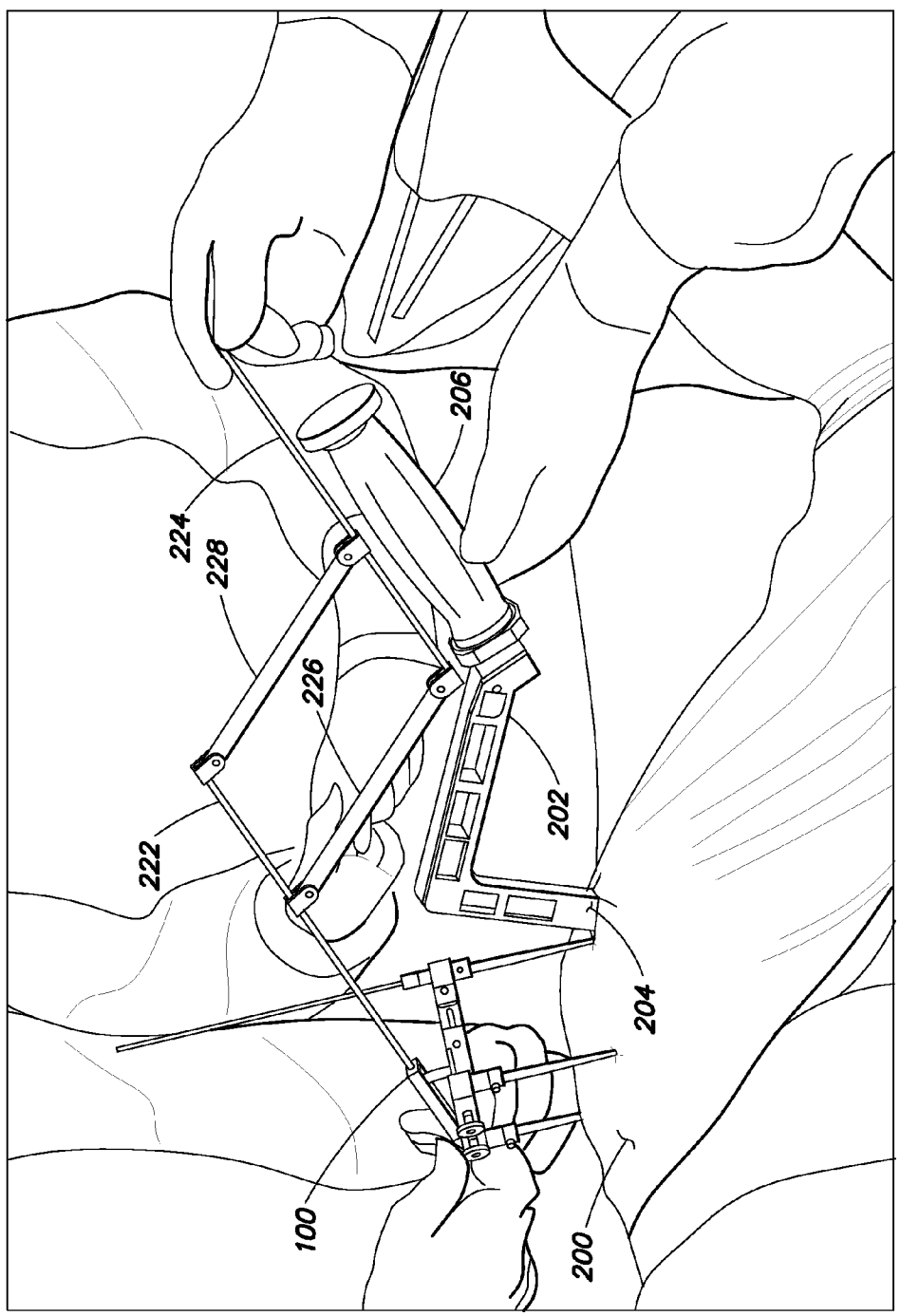
FIG. 4 is a pictorial view showing the parallel guide as used in conjunction with the stereotactic instrument of the '545 application during a surgical procedure.

FIG. 4 of the '545 application is reproduced here as FIG. 1 for ease of reference; the same reference numbers have been retained. It shows a preferred form of the manual stereotactic instrument of the '545 application. The manner in which that instrument is used to define a reference plane for arthroplastic surgery is described in detail in that application. For present purposes, it suffices to understand that the guide rod 128 defines the direction in which an acetabular cup is to be inserted into a hip.

Figure 2:
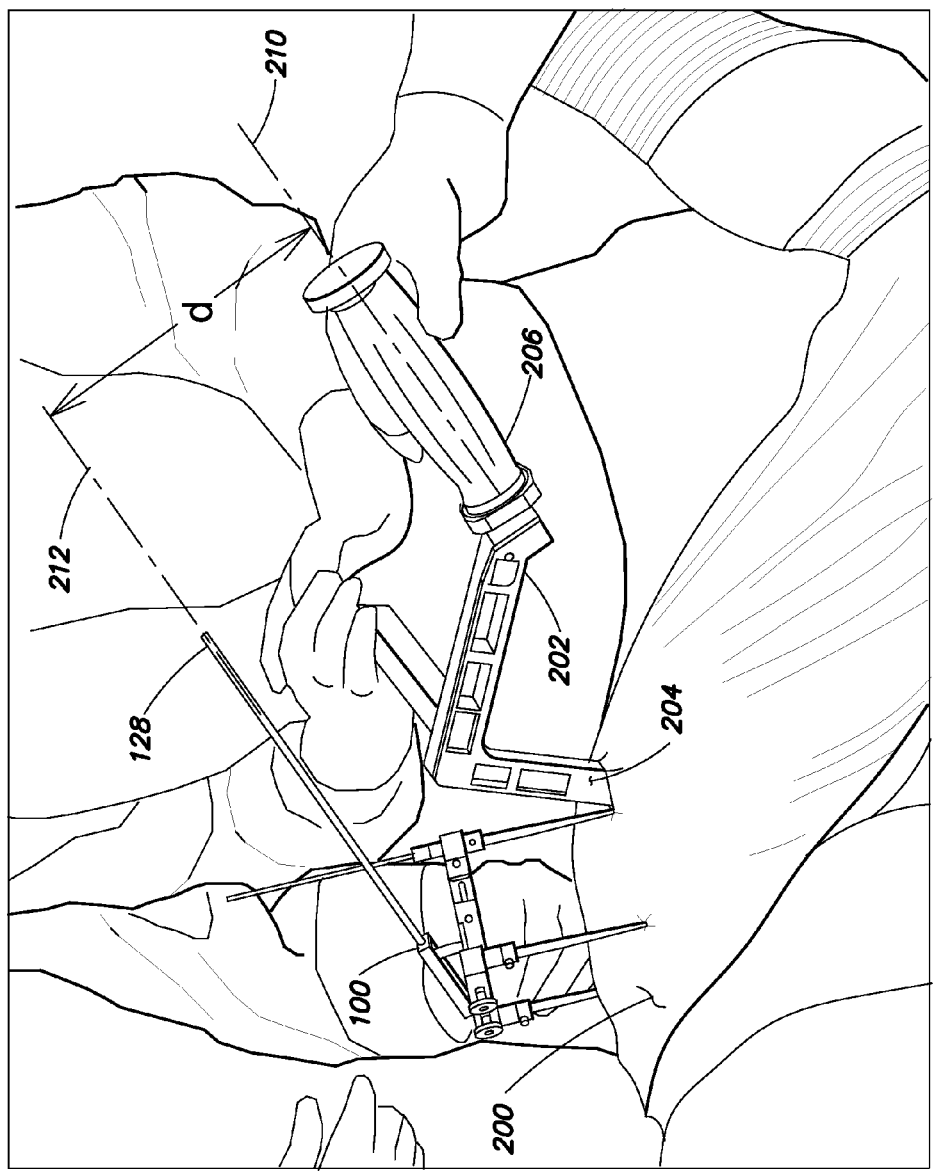
FIG. 2 is a pictorial view showing the manner in which a surgeon uses the stereotactic instrument to align an acetabular cup inserter

FIG. 2 shows the stereotactic instrument 100 positioned on a hip 200 during surgery. The guide 128 of the instrument, or an extension thereof, indicates the direction in which an acetabular cup is to be inserted. A cup inserter 202 of well known and commercially available type carries, at one end 204 thereof, an acetabular cup which is to be implanted in the patient; in FIG. 2, the cup is within the surgical incision and thus not visible. A handle 206 is formed at the other end of the inserter 202 to enable the surgeon to manipulate the cup and to apply a force to fix it in position when it has the desired orientation. The cup is releasably mounted on the inserter in a known orientation to the handle of the inserter. Thus, by positioning the handle with respect to the patient, the physician controls the angle at which the cup is inserted into the acetabulum.

As described in the '545 application, the guide 128 of the stereotactic instrument 100 enables the surgeon to establish the desired orientation of the cup. By aligning the handle 206 of the cup inserter with the guide 128, the surgeon can ensure that the cup is being positioned as desired. In particular, the surgeon visually aligns the axis 210 of the handle 206 parallel to the axis 212 of the guide 128. As can be seen from FIG. 2, the perpendicular distance "d" between the axis 210 of the handle 206 and the axis 212 of the guide 128 can be on the order of several inches, and this limits the ability of the surgeon to accurately judge parallel alignment.

In accordance with the present invention, I provide a simple method and apparatus for enhancing the accuracy of acetabular cup alignment in surgical procedures. The apparatus comprises a parallel guide that quickly and easily attaches to the instrument guide rod and that provides a second guide rod, parallel to the first, but positionable closer to the handle of the cup inserter so that the surgeon may accurately align the axis of the inserter with that of the instrument guide rod.

Figure 3:
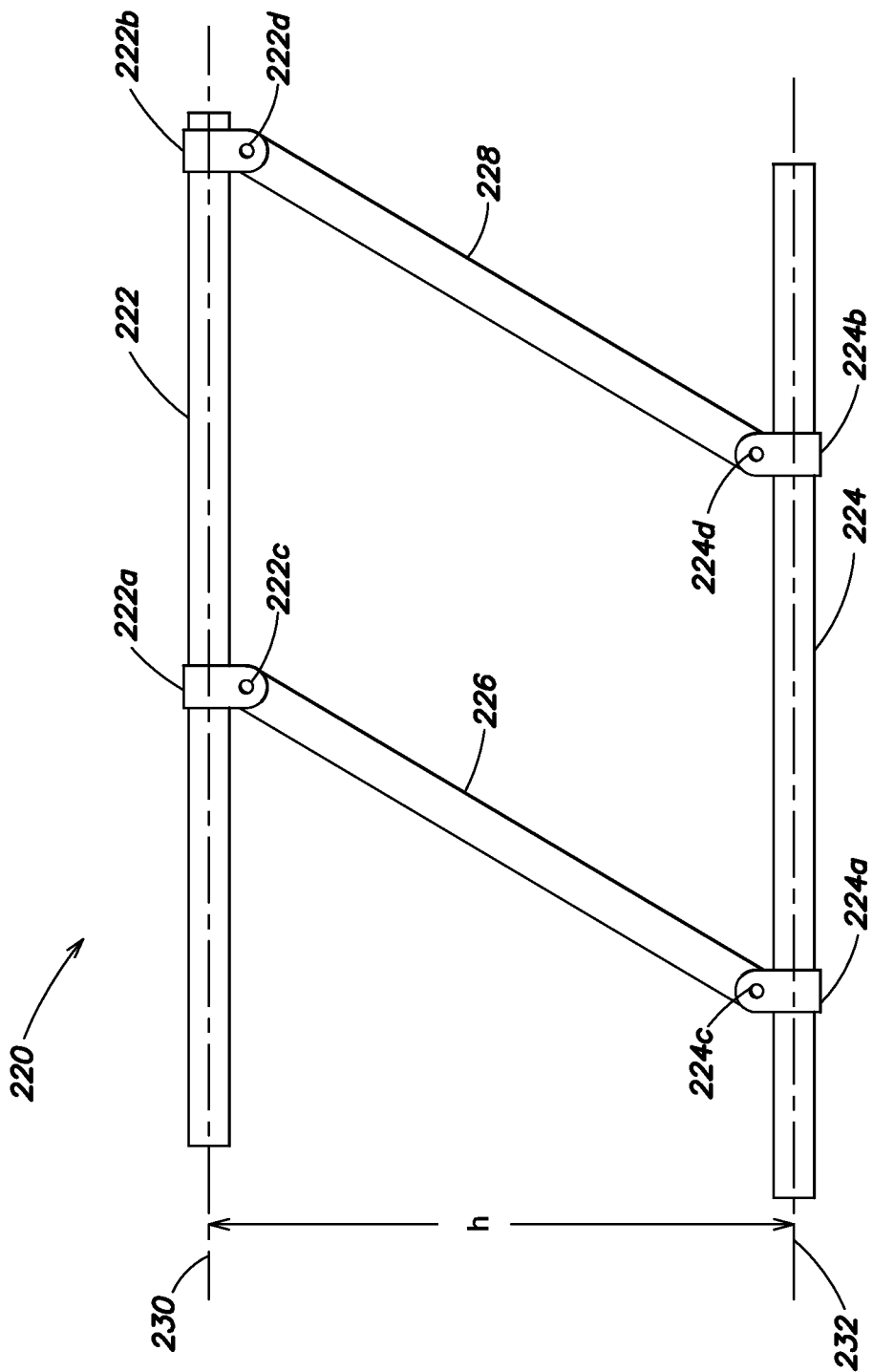
FIG. 3 is a plan view of the parallel guide of the present invention.

As shown in FIG. 3, the parallel guide 220 comprises a first arm 222 having first and second links 222a and 222b, respectively, and a second arm 224 having links 224a and 224b, respectively. The links 222a and 224a are pivotally connected by an arm 226, and the links 222b and 224b are pivotally connected by an arm 228. The arm 226 is rotatable about pin 222c in link 222a, as well as about pin 224c in link 224a. Similarly, the arm 228 is rotatable about pin 222d in link 222b, as well as about pin 224d in link 224b. The arms 226 and 228 are of equal length, and are mounted as shown such that the axis 230 of arm 222 and axis 232 of arm 224 are parallel and remain so despite the angular orientation of the arms 226 and 228 with respect to the arms 222 and 224. Thus, the perpendicular distance "h" between the axes 230, 232 of arms 222, 224, respectively, can be adjusted from a short distance (e.g., an inch or so) to a larger distance (e.g., six inches or so) while maintaining parallelism of the arms 222 and 224.

The arms 222, 224 may be of any convenient form, but advantageously comprise simple cylindrical tubing. One of the arms is adapted to fit onto the stereotactic instrument of FIG. 1. In a preferred embodiment, the attachment is accomplished by forming one of the arms, e.g., arm 222, from a hollow rod that snugly slides over the guide 128 of the instrument of FIG. 1. For example, if guide 128 is a cylindrical rod as shown in FIG. 1, then arm 222 is advantageously a hollow rod whose inside diameter is slightly larger that the outside diameter of the guide 128 so that it fits snugly thereon.

It is also desirable to control the extent to which the arm 222 slides over the guide 128. For example, if guide 128 has a shoulder 140 as shown in FIG. 1, then arm 222 can be slid over the guide until it butts against the shoulder. Alternatively, the length of arm 222 that can slide over guide 128 can be limited by means of an internal plug at a given distance along the length of the arm 222 that limits the penetration of the arm by the guide. It will be understood that other means for fastening the parallel guide 220 to the instrument guide 128 can be utilized. For example, guide 128 may be hollow and 222 constructed to slide into it. Alternatively, arm 222 may be connected to the guide 128 by means of clamps, spring-loaded, press-fit, or otherwise; by tape; or by other mechanical fastening means. Magnetic coupling may alternatively be employed to connect the two. As one example, guide 128 may be formed at least in part of magnetically susceptible material and arm 222 at least in part of magnetic material, or vice versa. The preferred form of connection described above, i.e., a sliding relationship between arm 222 and guide 128 has the advantage that the parallel guide can quickly be connected to, and disconnected from, the guide 128, a factor that is highly desirable in surgical procedures. This advantage is also provided by magnetic coupling and at least some forms of mechanical coupling.

FIG. 4 shows the parallel guide 220 mounted on the stereotactic instrument of FIG. 1. As can be seen, the lower arm 224 is parallel to the upper arm 222 but is considerably closer to the handle 206 of the cup inserter. Accordingly, the surgeon can now more accurately align the axis of the handle with the direction indicated by the guide 128.

The particular dimensions of the parallel guide will depend in part on the particular cup inserter that it is used with. For one type of commercially available cup inserter that is commonly used, the arms 222, 224 are on the order of nine inches in length and the arms 226, 228 are on the order of six inches in length, thus enabling the arms 222, 224 to spaced apart by up to six inches.

CONCLUSION

It will be understood that the foregoing description and drawings are directed to a preferred embodiment of the parallel guide of the present invention, and that other forms of the guide will readily be constructed from the description set forth herein, it being understood that the foregoing is intended as illustrative only, the scope of the invention being more fully defined in the claims appended hereto.

What is claimed is:

1. An apparatus comprising:
   a device for registering a pelvis, the device having
      a frame,
      first, second, and third legs extending from the frame, and
      a guide rod extending from the frame, the guide rod defining a set orientation in space relative to respective ends of the first, second, and third legs; and
   a parallel guide having
      first and second arms linked to each other by two or more cross arms which maintain the first and second arms in parallel relation to each other, the two or more cross arms being rotatably mounted on the first and second arms to enable the first and second arms to move toward or away from each other while maintaining a parallel relationship to each other, and
      means for attaching the first arm in a parallel relation to the guide rod of the device for registering the pelvis.

2. The apparatus of claim 1 wherein the means for attaching includes a hollow segment formed in the first arm for receiving the guide rod of the device for registering the pelvis to thereby establish the parallel relation between the first arm of the parallel guide and the guide rod of the device for registering the pelvis.

3. An apparatus for aligning an acetabular cup inserter to an set orientation in space, the apparatus comprising
   a hub;
   first and second arms extending from the hub;
   a first leg extending from the first arm;
   a second leg extending from the second arm;
   a third leg extending from the hub;

a direction guide extending from the hub, the direction guide defining the set orientation in space; and a parallel guide having first and second arms coupled to each other by two or more cross arms rotatably linking the first and second arms in parallel relationship to each other, and enabling the first and second arms to move toward or away from each other while maintaining the parallel relationship, and means for coupling the first arm of the parallel guide to the direction guide for alignment therewith whereby the set orientation in space defined by the direction guide may be replicated in the first arm of the parallel guide and thus in the second arm of the parallel guide.

4. The apparatus of claim 3 in which the first arm of the parallel guide has at least a hollow segment therein for receiving the direction guide therein.

5. The apparatus of claim 3 in which the first arm of the parallel guide is tubular.

6. The apparatus of claim 3 in which the first arm of the parallel guide is structured to slide over the direction guide.

7. The apparatus of claim 3 in which the first arm of the parallel guide is structured to slide within the direction guide.

8. A method comprising:

placing an end of a first leg of a device for registering a pelvis in the area of the posterior inferior acetabulum;

placing an end of a second leg of the device for registering the pelvis in the area of the anterior superior iliac spine;

placing an end of a third leg of the device for registering the pelvis on the ilium, the ends of the legs defining a plane, the device for registering the pelvis having a guide rod pointing in set orientation relative to the plane defined by the ends of the legs of the device for registering the pelvis; and attaching a parallel guide to the guide rod of the device for registering the pelvis, the parallel guide having a first arm that is parallel to and spaced from the guide rod of the device for registering the pelvis, wherein the parallel guide includes a second arm, and the attaching includes attaching the second arm of the parallel guide to the guide rod of the device for registering the pelvis.

9. The method of claim 8 wherein at least a portion of the second arm of the parallel guide is hollow, and the attaching the second arm of the parallel guide to the guide rod of the device for registering the pelvis includes sliding the second arm of the parallel guide over the guide rod.

10. The method of claim 8 wherein the parallel guide includes two or more cross arms that extend between the first arm and the second arm of the parallel guide.

11. The method of claim 10 wherein the two or more cross arms are pivotally attached to the first arm and the second arm of the parallel guide.

* * * * *